United States Patent [19]
Suzuki et al.

[11] Patent Number: 5,359,407
[45] Date of Patent: Oct. 25, 1994

[54] OPTICAL SCANNING APPARATUS, SURFACE-STATE INSPECTION APPARATUS AND EXPOSURE APPARATUS

[75] Inventors: Akiyoshi Suzuki; Michio Kohno, both of Tokyo, Japan

[73] Assignee: Canon Kabushiki Kaisha, Tokyo, Japan

[21] Appl. No.: 177,189

[22] Filed: Jan. 3, 1994

Related U.S. Application Data

[63] Continuation of Ser. No. 813,031, Dec. 24, 1991, abandoned.

[30] Foreign Application Priority Data

Dec. 28, 1990 [JP] Japan .................. 2-408924

[51] Int. Cl.⁵ .......................................... G01N 21/88
[52] U.S. Cl. ...................... 356/237; 250/572; 359/203; 359/204
[58] Field of Search ............. 356/237, 239, 240, 435; 250/561, 563, 572; 359/203, 204

[56] References Cited

U.S. PATENT DOCUMENTS

| | | | |
|---|---|---|---|
| 2,844,648 | 7/1958 | Rosenthal | 359/203 X |
| 3,646,568 | 2/1972 | Woywood | 359/203 X |
| 4,460,273 | 7/1984 | Koizumi et al. | 356/237 |
| 4,795,911 | 1/1989 | Kohno et al. | 250/572 |
| 4,886,975 | 12/1989 | Murakami et al. | 250/572 |

FOREIGN PATENT DOCUMENTS

62-188945 8/1987 Japan .

Primary Examiner—Vincent P. McGraw
Attorney, Agent, or Firm—Fitzpatrick, Cella, Harper & Scinto

[57] ABSTRACT

An optical system is arranged so that a scanning light beam for scanning a first region to be inspected and a scanning light beam for scanning a second region to be inspected are not simultaneously incident upon an object to be inspected. This prevents an adverse influence on the inspection caused by flare light generated when one scanning light beam is incident upon an edge of the object and is received by a light-receiving optical system for the region to be inspected scanned by another scanning light beam. The system includes two polygon mirrors provided as one body in an optical system at a position for projecting the light beams so that the distance between a focus point of the light beam projected on the lower surface of the object and a focus point of the light beam projected on the upper surface of the object in the beam scanning direction is greater than the width of the object in the beam scanning direction. As a result, the two light beams are alternately incident upon the object.

9 Claims, 11 Drawing Sheets

OPTICAL SCANNING APPARATUS, SURFACE-STATE INSPECTION APPARATUS AND EXPOSURE APPARATUS

This application is a continuation of application Ser. No. 07/813,031, filed Dec. 24, 1991, now abandoned.

BACKGROUND OF THE INVENTION

1. Field of the Invention

This invention relates to an optical scanning apparatus, a surface-state inspection apparatus and an exposure apparatus, and more particularly, to an optical scanning apparatus, a surface-state inspection apparatus, and an exposure apparatus using such apparatuses which are suitable for detecting a pattern defect, or a foreign particle, such as dust or the like, present on a substrate, such as a reticle, a photomask or the like (hereinafter generically termed a reticle) when they are used in a semiconductor production facility.

2. Description of the Related Art

In the IC (integrated circuit) production process, a circuit pattern for exposure formed on a reticle substrate is in general transferred onto the surface of a wafer coated with a resist using a semiconductor printing apparatus (a stepper or a mask aligner) to produce an IC.

At that time, if a foreign particle, such as dust or the like, is present on the surface of the substrate, the foreign particle is simultaneously transferred in a transfer operation and can cause a defective IC to be produced, thus causing a decrease in the yield of IC production.

Particularly when a circuit pattern is repeatedly printed on the surface of a wafer by a step-and-repeat method using a reticle, one foreign particle on the surface of the reticle is printed on the entire surface of the wafer, causing a great decrease in the yield of IC production.

Figure 1:
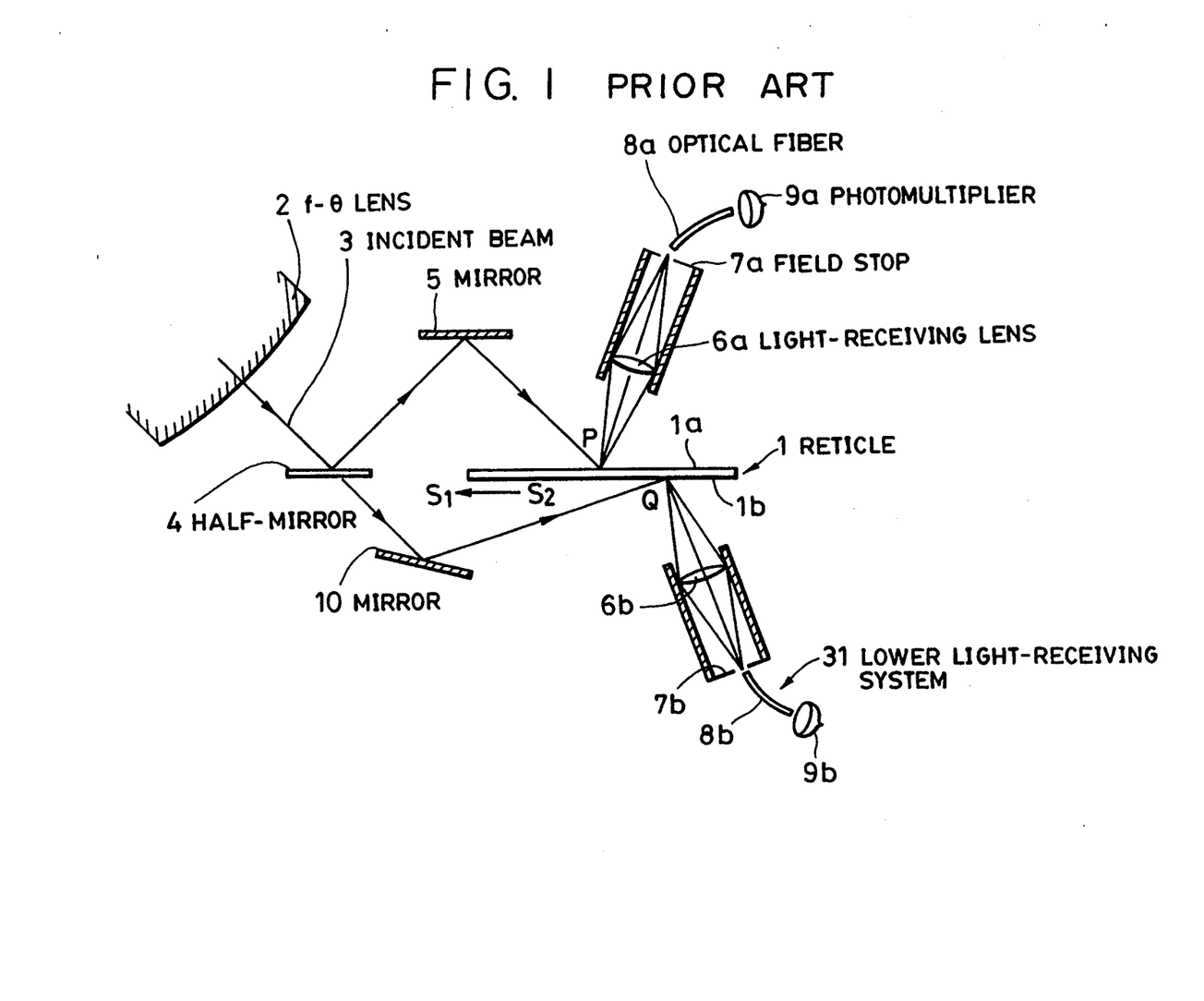
FIG. 1 is a diagram illustrating a conventional optical system.

Accordingly, it is important to detect the presence of a foreign particle on a substrate in the IC production process, and therefore various kinds of inspection apparatuses have been proposed. FIG. 1 shows an example of such an apparatus. Such an apparatus has been described in detail, for example, in Japanese Patent Public Disclosure (Kokai) No. 62-219631 (1987) (U.S. Pat. No. 4,886,975). This apparatus has a feature in that care is taken for shortening the inspection time compared with other conventional apparatuses. That is, an incident light beam 3 passing through an f-$\theta$ lens 2 is divided into two, i.e., upper and lower light beams by a half-mirror 4. These beams are condensed onto points P and Q on a substrate (reticle) 1 by reflecting mirrors 5 and 10, respectively. The reticle 1 has in general a surface having a circuit pattern at its lower side (1b) and a surface remaining as a glass blank at its upper side (1a). Only the pattern surface may be inspected when inspecting circuit defects, but the light beams must in some cases be incident on both the pattern surface and the blank surface when inspecting foreign particles, such as dust or the like.

A rotating element (polygon mirror, not shown) is provided in front of the f-$\theta$ lens 2, and scans the incident light beam 3 in a direction orthogonal to the plane of FIG. 1 by the rotation of the polygon mirror, whereby the upper and lower light beams scan the reticle surface in a direction perpendicular to the plane of FIG. 1. In order to inspect the entire reticle surface, the reticle 1 is moved in the direction from $S_2$ to $S_1$ in the plane of FIG. 1, whereby raster scanning is performed on the reticle surface. Scattered light issued from the incident point P on the reticle 1 is focused on a field stop 7a by the function of a light-receiving lens 6a. The field stop 7a guides only necessary signal light to an optical fiber 8a and a photomultiplier 9a in the following stage, and cuts out unnecessary flare light other than the signal light.

A light-receiving system 31 for scattered light issued from the incident point Q has the same configuration as described above. That is, a light-receiving lens 6b, a field stop 7b, an optical fiber 8b and a photomultiplier 9b have the same functions as described above.

As the size of a semiconductor chip is being further and further reduced, more accuracy is required for a reticle for producing these smaller semiconductor chips. Accordingly, a more precise inspection function than is available in the conventional art is required for a surface-state inspection apparatus for inspecting the reticle.

SUMMARY OF THE INVENTION

The present invention has been made in consideration of the above-described background, and is a modification of the above-described conventional approach.

It is an object of the present invention to provide a surface-state inspection apparatus which can detect a surface state with high precision while preventing the influence of flare light caused by scattering, particularly when light is incident on an end surface of a substrate with a simple configuration of a lens system.

In accordance with one aspect of the invention, an apparatus for optically scanning an object comprises light beam generation means for generating first and second light beams, and optical scanning means, including first and second rotating mirrors rotating as one body, for optically scanning the object. The first rotating mirror reflects the first light beam and the second rotating mirror reflects the second light beam, with the first and second light beams scanning the object by the rotation of the first and second rotating mirrors, and the first and second rotating mirrors being arranged so that the first and second light beams alternately scan the object.

In accordance with another aspect of the invention, an apparatus for inspecting a surface state of an object to be inspected comprises at least one light source emitting first and second light beams, and a scanning optical system including first and second rotating polygon mirrors rotating as one body, with the first rotating polygon mirror reflecting the first light beam and the second rotating polygon mirror reflecting the second light beam. The first and second light beams scan the object by rotation of the first and second rotating polygon mirrors, which are arranged so that the first and second light beams alternately scan at least part of the object to be inspected. In addition, a first detector detects light from the object scanned by the first light beam, with information relating to a surface of the scanned object being obtained as a result of the detection by the first detector, and a second detector detects light from the object scanned by the second light beam, with information relating to a surface of the scanned object being obtained as the result of the detection by the second detector.

The foregoing and other objects and features of the present invention will become more apparent from the

DETAILED DESCRIPTION OF THE PREFERRED EMBODIMENTS

Before explaining the particular embodiments of the present invention, a basic technique of the present invention will be explained with reference to the drawings for the purpose of better understanding of the principles underlying the subject invention.

Each of the elements shown in block outline in the drawings is well known per se, and no special type or construction of such elements is required to carry out the present invention.

Figure 2:
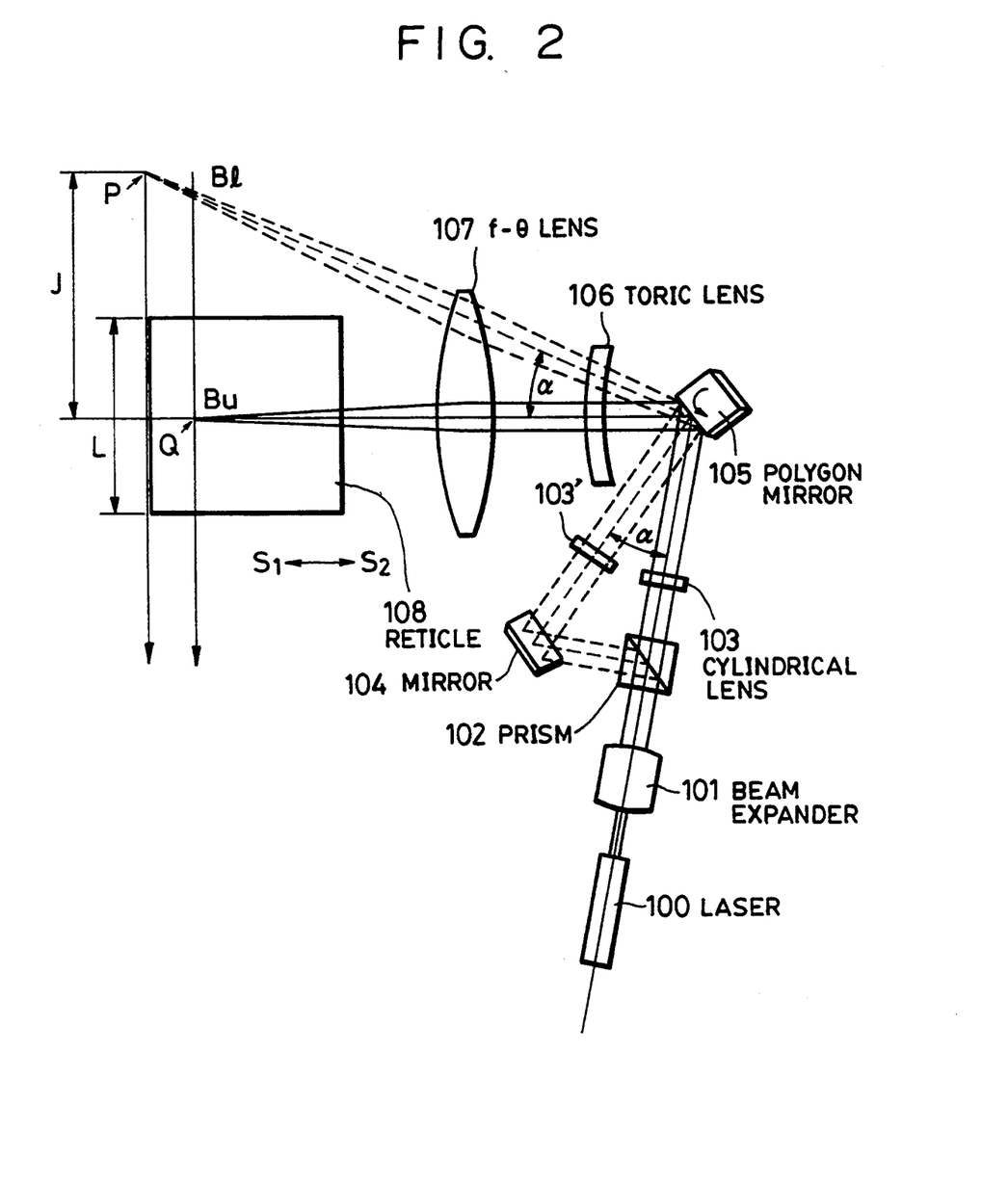
FIG. 2 is a top plan view of an optical system using a basic technique of the present invention.
Figure 3:
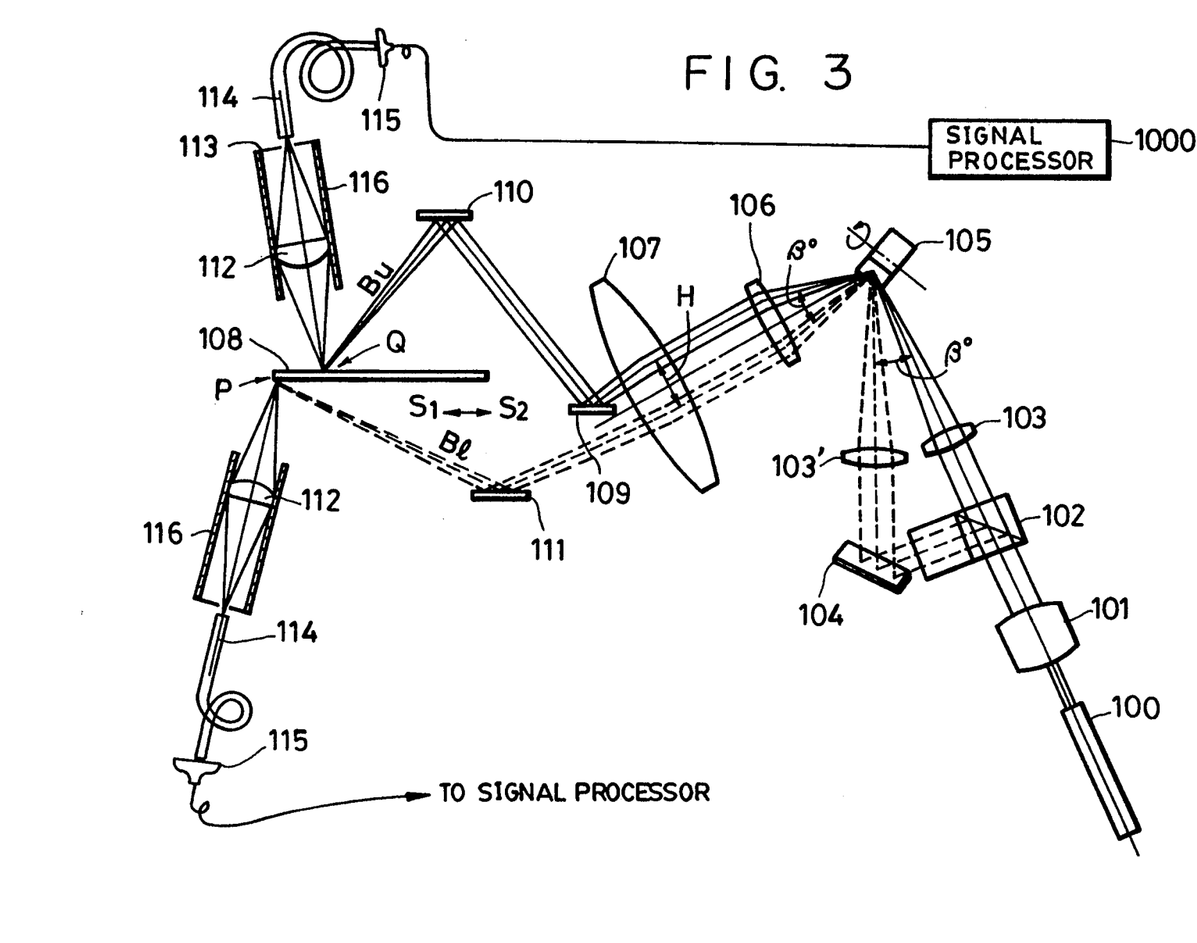
FIG. 3 is a side view of the system using the basic technique.

FIG. 2 is a top plan view of an optical system using a basic technique of the present invention, and FIG. 3 is a side view of the system. The configuration of the basic technique will be explained with reference to FIGS. 2 and 3.

A light beam emitted from a laser light source 100 is widened so as to have a predetermined light-beam diameter, and is incident upon a prism 102. The prism 102 has a half-mirror surface to transmit part of the light beam to a cylindrical lens 103, and to reflect the remaining light beam and guide it to another cylindrical lens 103' via a mirror 104. In practice, as shown in FIG. 3, the portion of the light beam reflected by the prism 102 is deflected by mirror 104 in a direction orthogonal to the plane of FIG. 2.

The optical axes of the cylindrical lenses 103 and 103' make angle α (degrees) with each other, and are incident upon a polygon mirror 105. In accordance with the rotation of the polygon mirror 105, the above-described two light beams are condensed on the upper and lower surfaces of a reticle 108 via a toric lens 106, an f-θ lens 107, and further via mirrors 109 and 110, and a mirror 111, respectively, while maintaining the angle α, and scan the reticle surface in a direction perpendicular to the plane of FIG. 3, and i.e., in an up-and-down direction in FIG. 2.

The mirrors 109–111 for guiding the light beams to the upper and lower surfaces of the reticle 108 are omitted in FIG. 2. As described above, this optical system simultaneously scans the two light beams on the upper and lower surfaces of the reticle 108 to be inspected. At the same time, by scanning the reticle 108 in a direction ($S_1$-$S_2$ direction) orthogonal to the scanning direction of the light beams using a stage (not shown), the entire surface of the reticle 108 is subjected to raster scanning to inspect its surface state. This optical system introduces an inclination correction system in order to avoid the influence by surface deviation of the polygon mirror 105. The prism 102 emits the light beam reflected by its built-in half-mirror in a direction orthogonal to the scanning cross section of the beam (within the plane of FIG. 3) in a state of being deviated. This light beam is incident upon the polygon mirror 105 at an angle β (degrees) with the transmitted light beam via the mirror 104 and the lens 103'. The two light beams reflected by the polygon mirror 105 are also incident upon the scanning lens (the toric lens 106 and the f-θ lens 107) at angle β. If the synthesized focal length of the scanning lens is represented by f, the two beams issued from the f-θ lens 107 advance separated by an amount H of deviation determined by:

$$f \times \pi/180 \times \beta = H \quad (1)$$

when the lens 107 is an f-θ lens, or $$f \times \tan \beta = H \quad (2)$$

when the lens 107 is a usual lens.

The upper beam Bu is condensed on a point Q on the upper surface of the reticle 108, and the lower beam Bl is condensed on a point P on the lower surface of the reticle 108.

According to the above-described configuration, the upper and lower beams Bu and Bl are completely separated within the cross sections of FIGS. 2 and 3. Hence, scattered light generated at an edge of the reticle 108 by one light beam will never be incident upon a detection system for another light beam directly.

If a foreign particle is present within an inspection area, for example, on the upper surface of the reticle 108, scattered light generated when scanning light is incident upon the foreign particle is condensed by a lens 112 provided within the light-receiving optical system shown above the reticle 108 in FIG. 3, and is refocused on an aperture of a field stop 113. Subsequently, the scattered light is guided to a photomultiplier 115 by an optical fiber 114. These components constitute the light-receiving optical system. The output of the photomultiplier 115 is processed by an electric processing system in the following stage, which system issues a signal indicating the presence of a foreign particle. Light-receiving optical systems are provided for the upper and lower light beams Bu and Bl, respectively. Accordingly, the same processing as described above is performed also when a foreign particle is present on the lower surface of the reticle 108. A cylindrical lens, a spherical lens, a group of bar lenses, a Selfoc lens array (made of optical fibers having graded refractive indices) or the like may be used as the lens. The above-described light-receiving optical system is configured so as to be able to receive scattered light from the entire scanning region in one scanning operation. The rotational angle of the polygon mirror 105 and the position of the reticle stage are always detected by detectors (not shown), whereby the scanning position of each scanning light beam on each surface to be inspected is monitored. The state of each surface, such as a position where a foreign particle adheres or the like, is detected by a signal processor 1000 from the above-described information and the output of the photomultiplier 115. In FIG. 2, the light-receiving optical systems and the like are omitted. In order to detect only scattered light from a foreign particle on a surface to be inspected having a pattern, such as the lower surface of a reticle, the configuration described, for example, in Japanese Patent Public Disclosure (Kokai) No. 62-188945 (1987) may be adopted.

If it is assumed that the light beam Bl is condensed on the point P on the lower surface of the reticle 108 and the light beam Bu is condensed on the point Q on the upper surface of the reticle 108 when the rotation of the polygon mirror 105 is stopped, the distance J between the points P and Q in the beam scanning direction (the up-and-down direction in FIG. 2) is arranged to be longer than the length L of the side of the reticle 108 in the beam scanning direction. Accordingly, scanning of the surface to be inspected by the respective beams is alternately performed. Hence, as the reticle stage moves in the $S_1$-$S_2$ direction and the lower beam Bl reaches a position for scanning the upper edge of the reticle 108, the upper beam will be disposed at a position outside of the reticle. Likewise, the lower beam Bl does not scan the reticle edge while the upper beam Bu inspects the upper surface of the reticle 108, as shown in FIG. 2. Accordingly, since the light beams Bl and Bu alternately scan the reticle 108, flare is not generated by one light beam to interfere with the receiving optical system of the other light beam.

Figure 4:
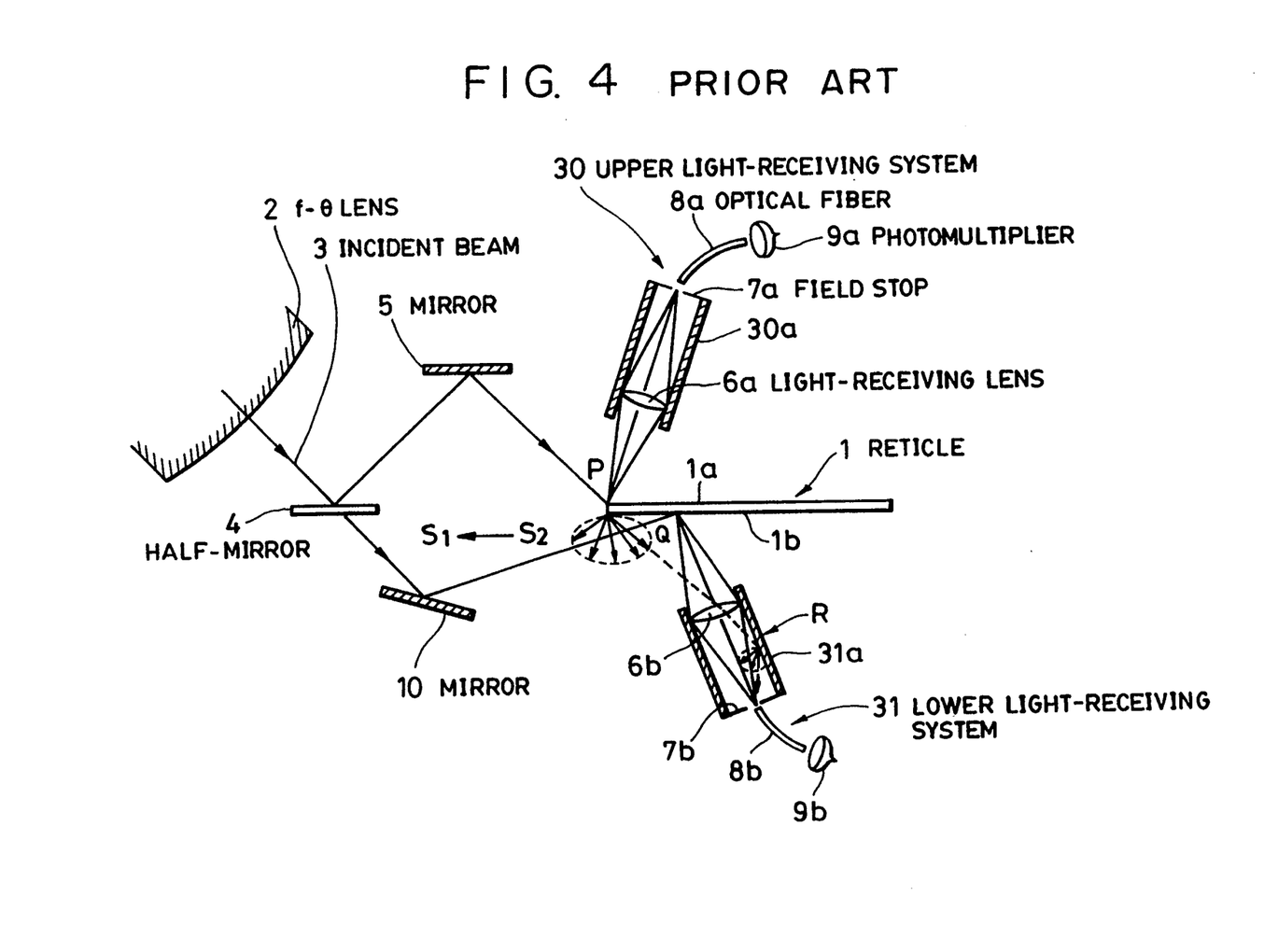
FIG. 4 is a diagram illustrating a comparative optical system.

The above-described relationship will be explained with reference to FIG. 4 showing a comparative optical system. FIG. 4 represents a time period when the upper beam reaches the left edge of the reticle 1 while the reticle 1 moves from the right to the left in the apparatus shown in FIG. 1. At that time, the lower beam is already near the center of the reticle 1, and the detection system 31 is receiving signal light from the lower surface of the reticle 1.

Since an edge surface of a substrate, such as a reticle or the like, is coarse, strong scattered light is directed in substantially all directions if a laser light beam irradiates the edge surface. At that time, the edge scattered light is, of course, also incident upon the light-receiving system 30 above the upper surface of the reticle. However, since the light beam at the upper surface is not yet in a region to be inspected, the scattered light is not received in the processing system as an electric signal. Hence, no problem arises. However, the edge scattered light is also incident upon the light-receiving system 31 at the lower-surface side of the reticle 1 in the following manner.

Since the light-receiving system 31 (in the same manner as the system 30) has the field stop 7b, basically, only scattered light (signal light) from the light-issuing point Q on the reticle 1 is guided to the photomultiplier 9b. However, in the case of strong scattered light, such as the edge scattered light, if the scattered light is incident upon a cylinder 31a (or the edge of the lens 6b or the like) of the light-receiving optical system 31, the incident point R functions as a secondary light source and generates new scattered light (flare) within the light-receiving optical system. The scattered light (indicated by broken lines in FIG. 4) passes through the field stop 7b, and reaches the photomultiplier 9b via the optical fiber 8b to be photoelectrically detected.

A foreign particle, such as dust or the like, to be detected on the reticle surface has the size of 1 $\mu$m to 5 $\mu$m. The intensity of the above-described scattered light from the reticle edge, even though secondary scattered light, is in some cases equal to or greater than the intensity of scattered light generated by such a fine particle. As a result, even if no foreign particle or defect is present at the point Q, serving as an actual point to be inspected, the system may erroneously react as if a foreign particle or defect were detected, and reliability in inspection of the lower surface of the reticle may be reduced.

To the contrary, the present invention has the above-described configuration wherein, while one of the light beams (the light beam Bu in the case of FIGS. 2 and 3) scans the corresponding surface to be inspected (the upper surface of the reticle in the case of FIGS. 2 and 3), that is, during the inspection period, another light beam (the light beam Bl in the case of FIGS. 2 and 3 reaching a position for scanning the edge portion of the reticle 1 is not present on the reticle 1. Hence, the above-described flare is not produced. Subsequently, when the other light beam (the light beam Bl in the case of FIGS. 2 and 3) reaches the reticle 1 and scans the edge portion by the rotation of the polygon mirror 105, if flare is generated in the light-receiving optical system (the upper-side light-receiving optical system in the case of FIG. 3) for inspecting the surface which the one light beam scans, as described in the comparative system, the one light beam (the light beam Bu in the case of FIGS. 2 and 3) is not on the surface to be inspected (the upper surface of the reticle 1), that is, not in the course of performing inspection. Even if an output is transmitted from the photomultiplier 115 to the signal processor 1000 in this state, the output can be clearly discriminated from the signal. Since the position of the scanning light beam on each surface to be inspected (that is, whether or not each scanning light beam is present on each surface) is monitored, an output from the corresponding photomultiplier 115 may be received in the signal processor 1000 only when each light beam is present on each surface to be inspected.

The situation is the same also when the one light beam (the light beam Bu in the case of FIGS. 2 and 3) reaches a position for scanning the edge portion of the reticle 1.

As described above, since the two light beams alternately scan the respective surfaces to be inspected, it is possible to prevent misdetection caused by flare.

If the composite focal length of the beam scanning system (the toric lens 106 and the f-$\theta$ lens 107) is represented by f, the following relationship holds among $\alpha$, J and L in FIG. 2:

$$f \times \pi/180 \times \alpha = J > L \qquad (3).$$

In general, the lens 107 need not necessarily have the f-$\theta$ characteristic provided that electrical correction or the like is performed. Although dependent on the distortion correction method, in the case of a usual corrected lens, expression (1) is replaced by:

$$f \times \tan \alpha = J > L \qquad (4).$$

In the above-described system, the upper and lower light beams are deviated substantially symmetrically with respect to the optical axis of the scanning lens. In another approach, for example, the lower light beam Bl may pass on the optical axis of the scanning lens, and only the upper light beam Bu may be deviated. In general, aberration can be more easily corrected and hence a light beam can be more easily focused on a reticle if an optical system is designed on its axis. On the other hand, a circuit pattern is usually provided on the lower surface of the reticle and is inspected. Hence, higher foreign-particle detection capability is required for the lower surface than for the glass surface (the upper surface). Accordingly, if the lower light beam passes on the optical axis of the scanning lens, scanning and inspection can be performed by a finer light beam. As a result, it is possible to perform more precise inspection for the lower surface of the reticle.

In the following embodiments of the present invention, a smaller angle for two light beams incident upon a polygon mirror than in the above-described basic technique is provided for the purpose of providing a smaller optical system.

Figure 5:
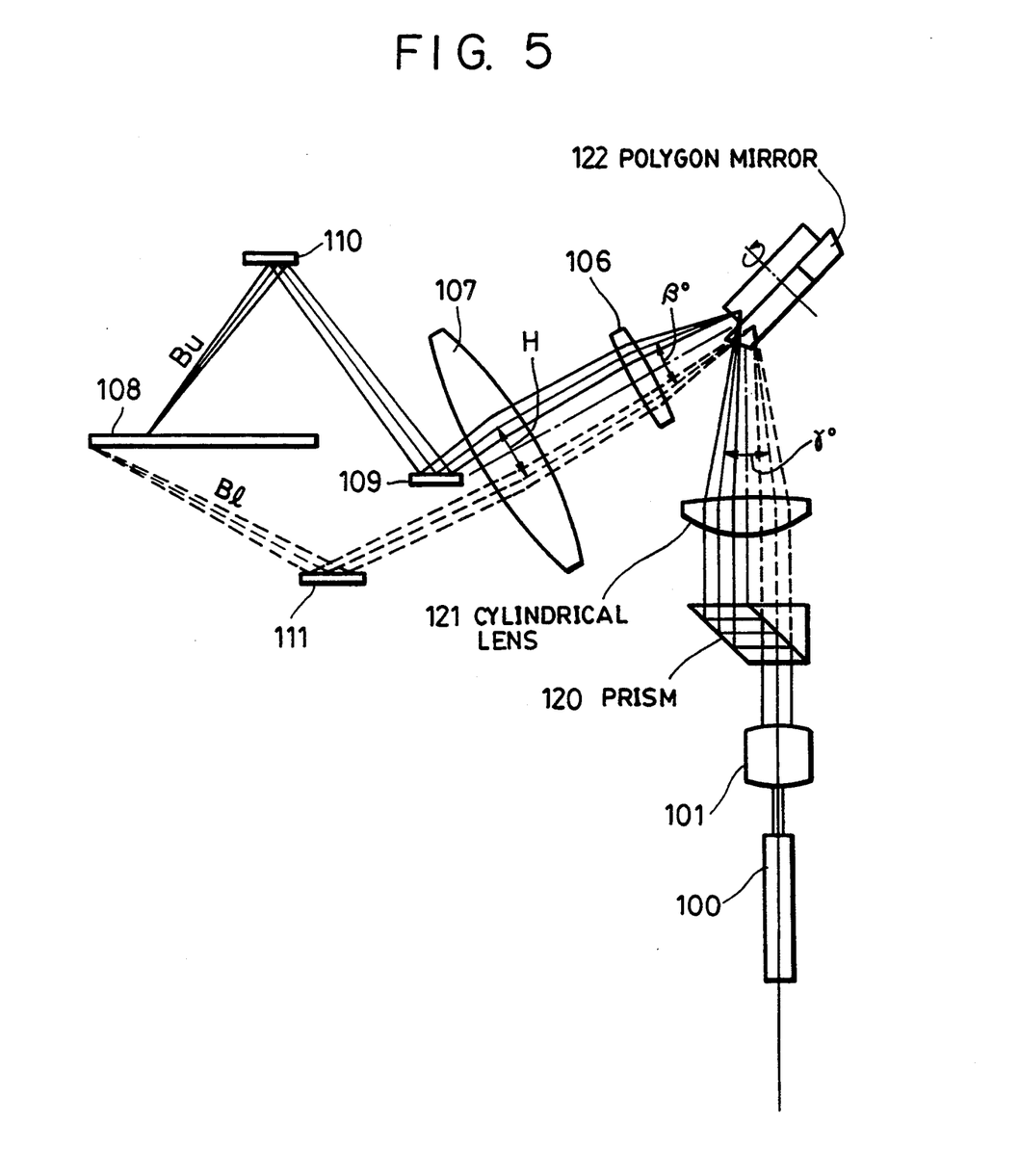
FIG. 5 is a side view of an optical system according to a first embodiment of the present invention.

FIG. 5 is a side view of an optical system according to a first embodiment of the present invention. In the following embodiments, like components as those described above are indicated by like reference numerals, and an explanation thereof will be omitted. Light-receiving optical systems and signal processors will be also omitted.

In the above-described basic technique, as shown in FIGS. 2 and 3, the prism 102, the mirror 104 and the cylindrical lens 103' are provided in order to provide an angle difference (the angle $\alpha$ in the beam scanning surface and the angle $\beta$ in the surface orthogonal to the scanning surface) between the two light beams. On the other hand, the present embodiment has a feature in that a smaller optical system (a prism 120 and a cylindrical lens 121) than the optical system used in the above-described basic technique is provided by providing two polygon mirrors affixed as one body in a state of being shifted in the direction of rotation FIGS. 6A and 6B show the polygon mirrors used in the present embodiment.

Figures 6A, 6B:
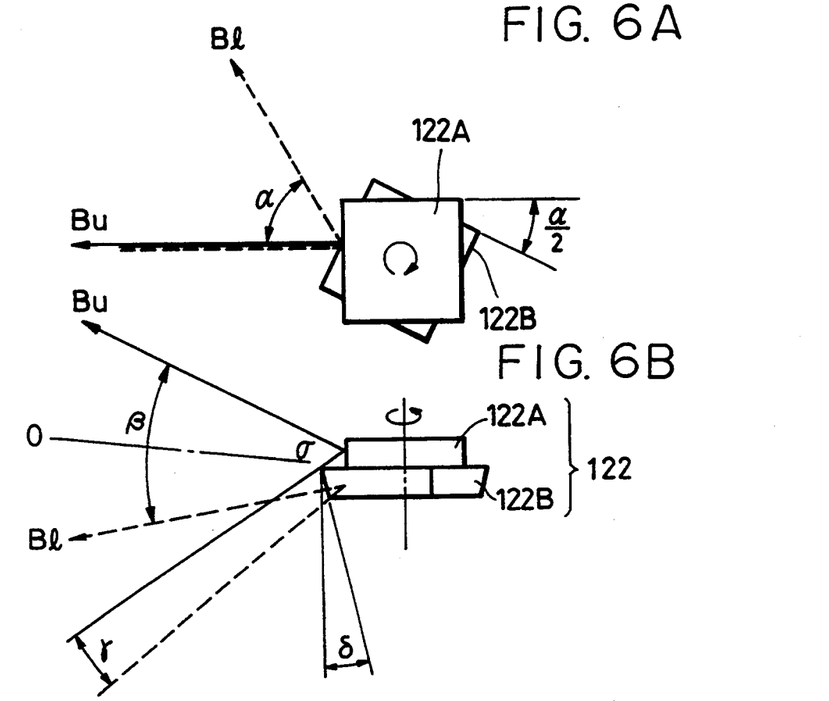
FIGS. 6A and 6B are diagrams illustrating a polygon mirror used in the first embodiment.

FIG. 6A is a diagram showing the polygon mirrors in their plane of rotation, that is, a top plan view of the polygon mirrors. Two tetrahedral polygons having the same shape are affixed together in a state of being rotated by an angle $\alpha/2$. If the upper light beam Bu and the lower light beam Bl are incident from the same direction, the light beam Bu incident upon the upper polygon (122A) returns to the incident direction, while the light beam Bl incident upon the lower polygon (122B) is reflected in a direction of an angle $\alpha$. As explained with reference to FIG. 2, the angle $\alpha$ may have any value provided that expression (3) or (4) is satisfied.

FIG. 6B is a diagram showing the polygon mirrors in a plane orthogonal to the plane of rotation, that is, a side view of the polygon mirrors. The reflecting surface of the lower polygon 122B is inclined by an angle $\delta$(degrees) with respect to the axis of rotation. In the present embodiment, the reflecting surface of the upper polygon 122A need not be particularly inclined. By intentionally providing such surface inclination, it is possible to freely select the amount H of deviation between the upper and lower light beams explained with reference to FIG. 2. If an angle between two main incident light beams on the polygons is represented by $\gamma$ (degrees), the following expression holds:

$$\gamma + 2\delta = \beta \qquad (5).$$

Referring again to FIG. 5, the prism 120 and the cylindrical lens 121 function as follows. That is, the prism 120 incorporates a half-mirror which deflects a reflected light beam relative to a transmitted light beam, and the reflected and transmitted light beams are emitted from the prism in parallel. The cylindrical lens 121 has the function of transmitting the two light beams symmetrically with respect to the optical axis, and condensing the beams on the surface of the composite polygon mirror 122 in the plane of FIG. 5.

According to the configuration of the present embodiment, the angle between the beams may be determined by the arrangement of the components, not by adjusting the optical axis of mirrors and the like. Hence, it is possible to increase accuracy.

Figure 7:
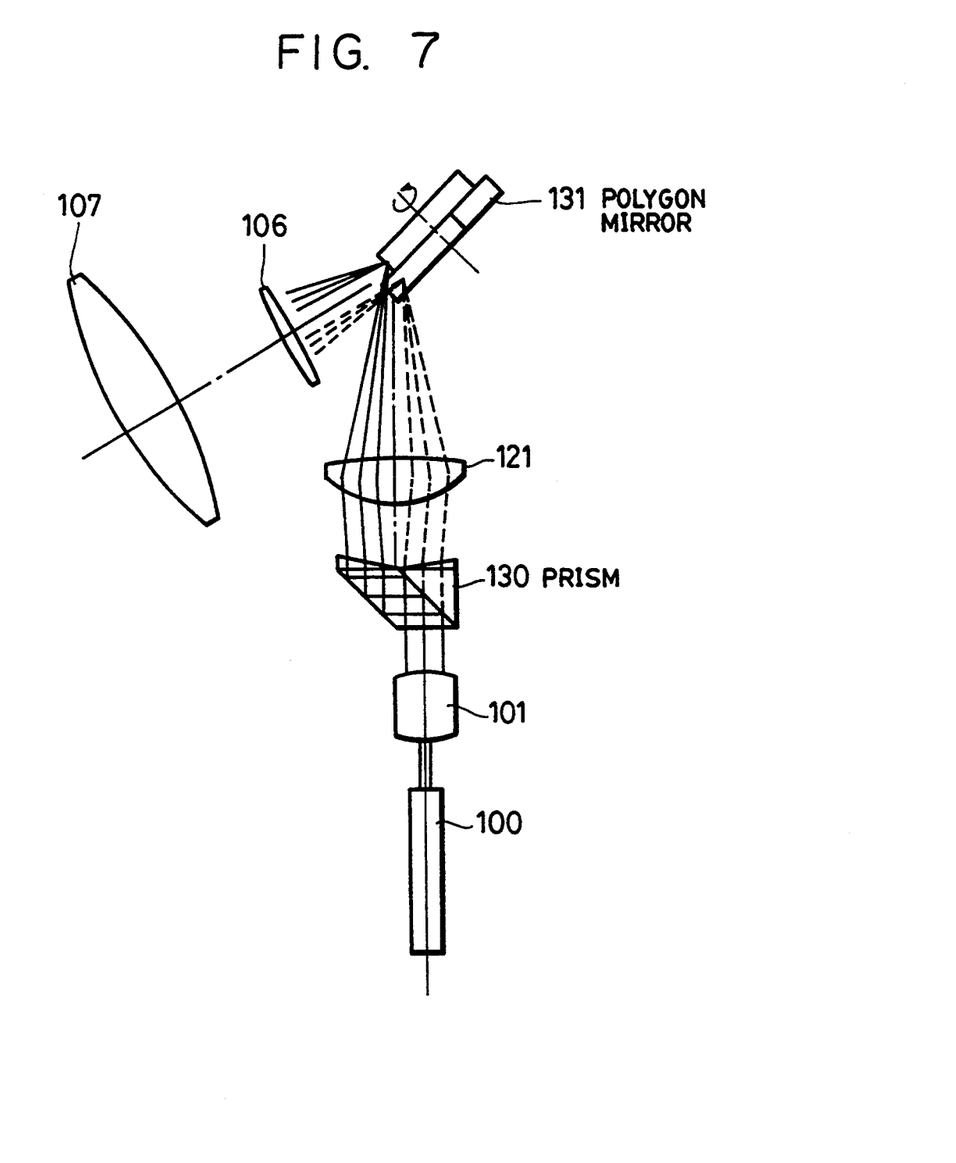
FIG. 7 is a side view of an optical system according to a second embodiment of the present invention.

FIG. 7 is a side view of part of an optical system according to a second embodiment of the present invention. Since other components are the same as in the first embodiment, an explanation thereof will be omitted. In the first embodiment, the surface of the polygon mirror is intentionally inclined for the purpose of providing a deviation between the two beams. In the present embodiment, a prism 130 is provided in order to provide a deviation between light beams. The prism 130 has the configuration of attaching a bar-like glass member on the beam issuing portion of the prism 120 shown in FIG. 5, and has the function of inclining light beams. According to this configuration, a deviation between the light beams is provided in the same manner as when the surface of the polygon mirror is inclined.

Figure 8:
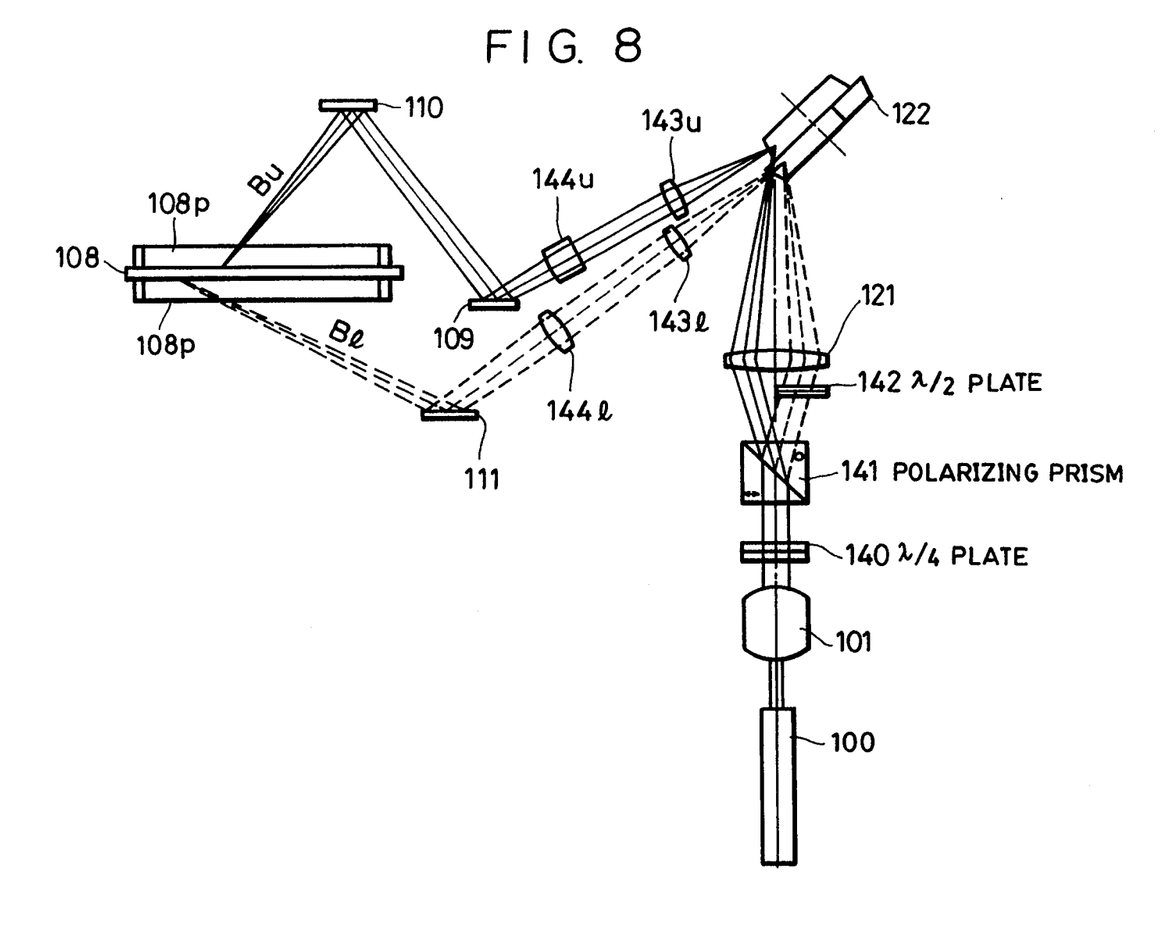
FIG. 8 is a side view of an optical system according to a third embodiment of the present invention.

FIG. 8 is a side view of an optical system according to a third embodiment of the present invention. A first feature of the present embodiment is in that a $\lambda/4$ plate 140, a polarizing prism 141 and a $\lambda/2$ plate 142 are placed between the beam expander 101 and the cylindrical lens 121. A second feature of the present embodiment is in that while the scanning lens (the toric lens and the f-$\theta$ lens) is used as a deviation providing system in the foregoing embodiments, separate lens systems are provided for upper and lower light beams in the present embodiment. In FIG. 8, there are shown f-$\theta$ lenses 144$u$ and 144$l$, and toric lenses 143$u$ and 143$l$. The main light beam of each of the upper and lower light beams passes through the optical axis of each of these lens systems. A reticle 108 with dustproof pellicles affixed thereto is illustrated as an object to be inspected.

The functions of the optical elements 140–142 will now be explained.

A linearly-polarized-light laser is used as the laser 100. The laser beam passing through the beam expander 101 and the $\lambda/4$ plate 140 (its optical axis is set in the direction of 45° with respect to the polarizing plane of the incident laser light) becomes a circularly polarized light. The polarizing prism 141 for receiving this circularly polarized light is a double-image element, such as a Wallaston prism or a Rochon prism, and is made by connecting two apex-angle prisms having the same apex angle with their optical axes orthogonal to each other. The polarizing prism 141 is made of birefringent crystals. Hence, when the circularly polarized light is incident, light output from the polarizing prism 141 is divided into ordinary rays and extraordinary rays (represented by solid lines and broken lines in FIG. 8, respectively) due to birefringence.

The same cylindrical lens 121 as that shown in FIG. 7 is used, and the optical path in the following stage is basically the same as in the foregoing embodiments except that a homocentric scanning lens system is used.

Finally, the function of the $\lambda/2$ plate 142 will be explained.

The polarizing planes of the two beams issued from the polarizing prism 141 are orthogonal to each other. In the case of FIG. 8, the light represented by solid lines (Bu) has its polarizing plane in the plane of FIG. 8, and is incident upon the reticle 108 in the form of P-polarized light. On the other hand, the polarizing plane of the light represented by broken lines (Bl) is orthogonal to that of the above-described light, and would be incident upon the reticle 108 in the form of S-polarized light if the $\lambda/2$ plate 142 were not present.

A case of inspecting the reticle 108 having the pellicles 108p will now be considered. As shown in FIG. 8, if the light beam is obliquely incident upon the pellicle surface, the energy of the light beam reaches the surface of the reticle 108 without being lost in the case of P-polarized light since transmissivity is high. On the other hand, in the case of S-polarized light, most of the energy of the light beam is lost by reflection at the pellicle surface since reflectivity is high, and a necessary amount of the light beam does not reach the surface of the reticle 108. Furthermore, the amount of transmitted light is greatly influenced by variations in the thickness of the pellicle.

In order to solve the above-described problem, the $\lambda/2$ plate 142 is placed in the optical path (the $\lambda/2$ plate 142 may be placed at a position other than the position shown in FIG. 8) so as to set its optical axis in the direction of 45° with respect to the plane of FIG. 8. As a result, the issued light beam is incident upon the reticle 108 in the form of P-polarized light.

In the present embodiment, the $\lambda/4$ plate 140 is unnecessary if the laser 100 emits randomly polarized light. The $\lambda/2$ plate 142 is also unnecessary when a substrate not having pellicles is inspected or when inspection is intentionally performed with S-polarized light.

Figure 9:
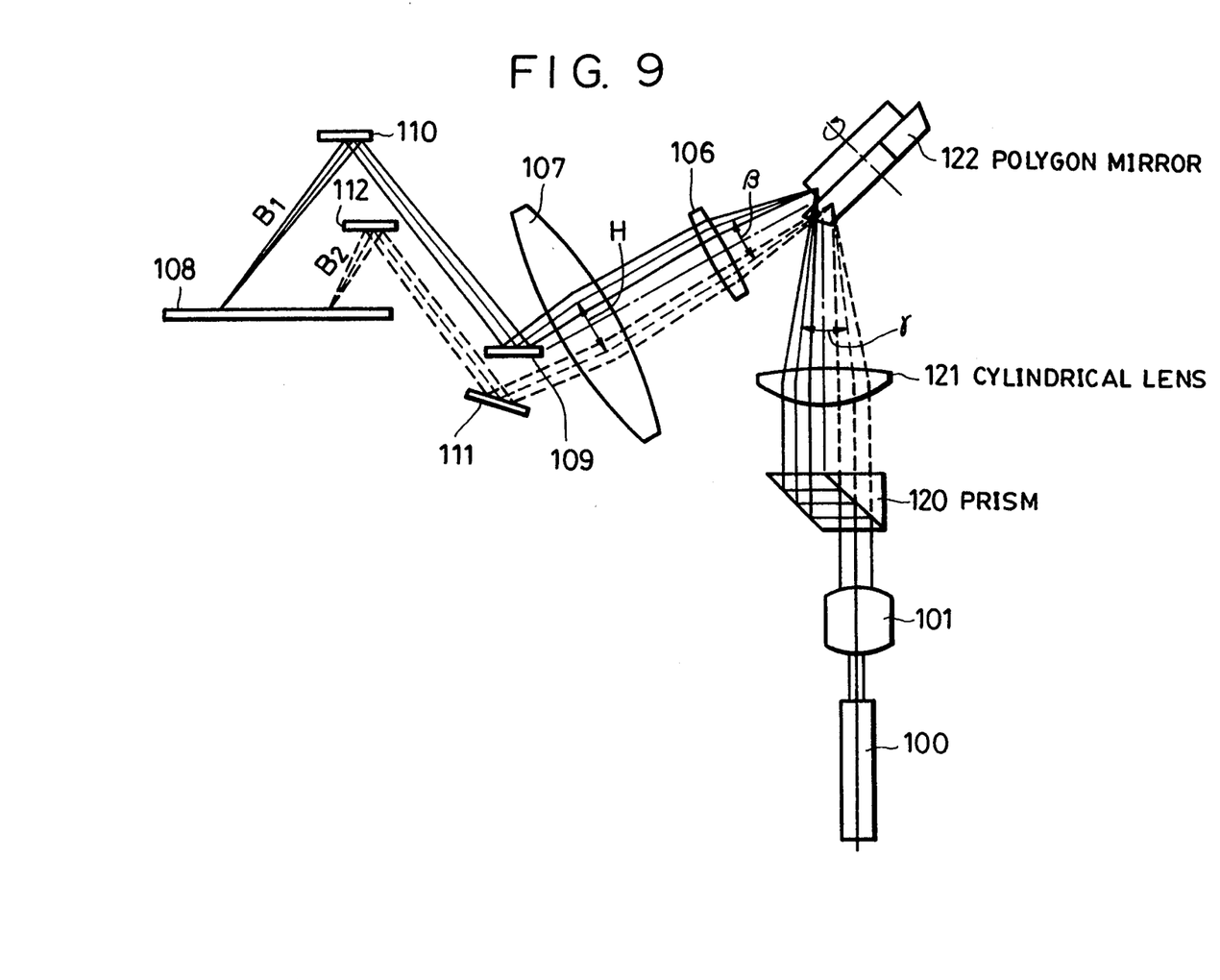
FIG. 9 is a side view of an optical system according to a fourth embodiment of the present invention.

FIG. 9 is a side view of an optical system according to a fourth embodiment of the present invention. The system shown in FIG. 9 has substantially the same configuration as that of the system shown in FIG. 5, but differs in that two beams are incident upon the upper surface of the reticle 108 by adding mirrors 111 and 112. As in this case, regions to be inspected by respective beams may be provided on the same surface. Alternatively, the same region may be inspected by respective beams.

The present embodiment may be applied not only to a transparent substrate, but also to an opaque substrate, such as a Si wafer.

Figure 10:
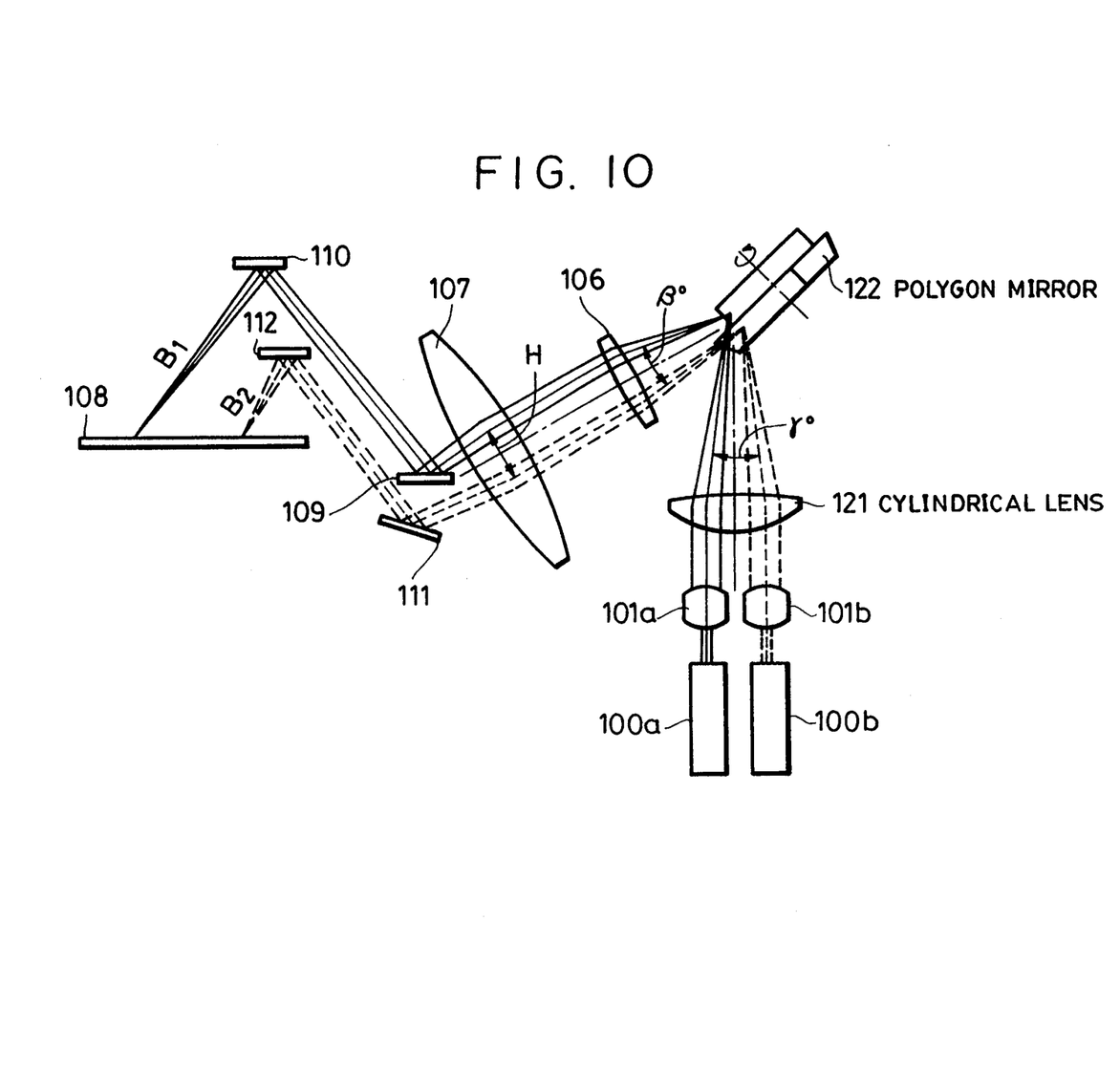
FIG. 10 is a side view of an optical system according to a fifth embodiment of the present invention.

FIG. 10 is a side view of an optical system according to a fifth embodiment of the present invention.

The optical systems of the foregoing embodiments may, of course, be configured using a plurality of lasers. FIG. 10 represents an example of such a case. The optical system shown in FIG. 10 differs from the optical system shown in FIG. 9 only in that two light sources 100a and 100b and two beam expanders 101a and 101b are provided.

Figure 11:
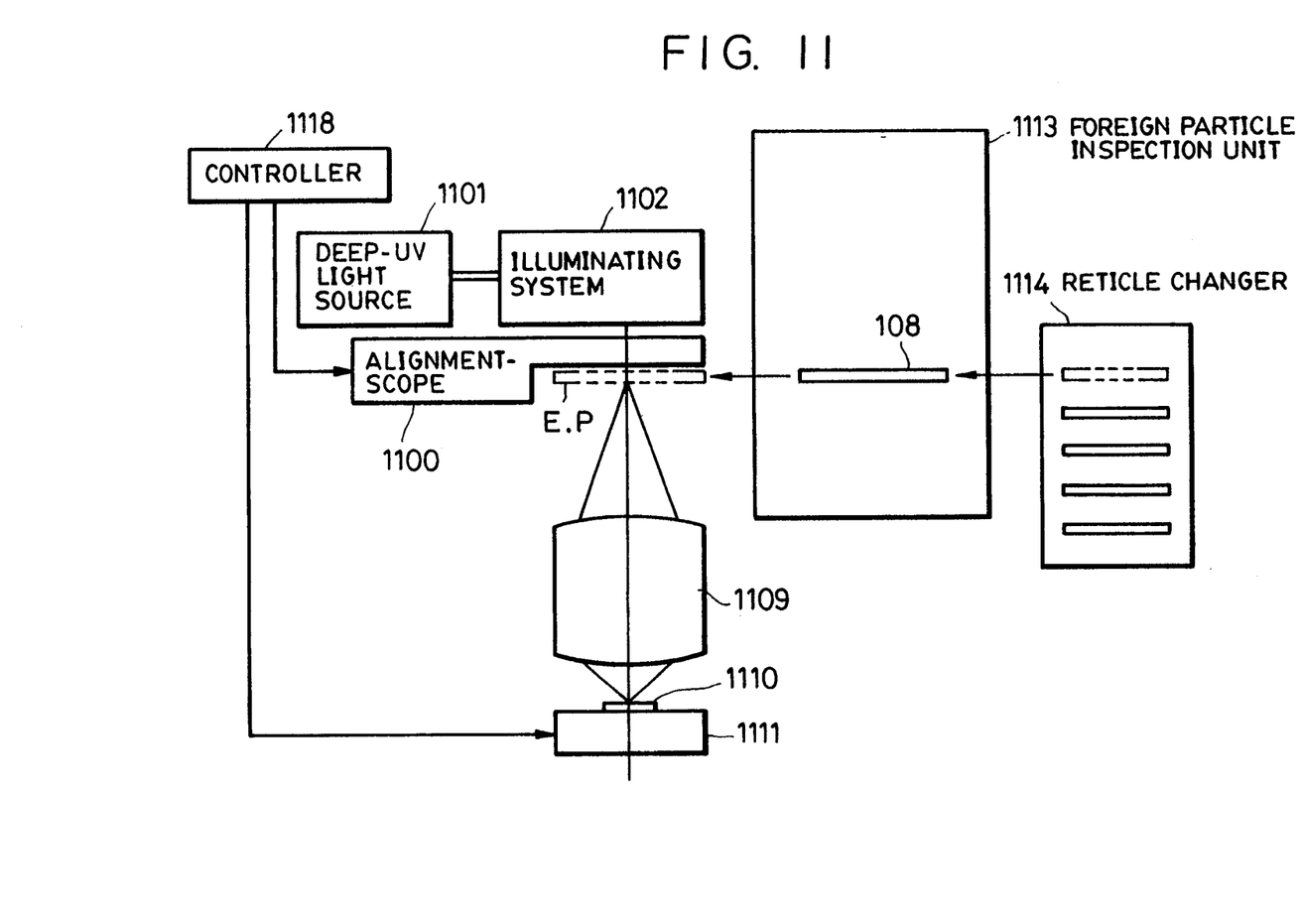
FIG. 11 is diagram showing the configuration of an apparatus according to a sixth embodiment of the present invention.

FIG. 11 is a diagram showing the configuration of a surface state inspection apparatus according to a sixth embodiment of the present invention. In the present embodiment, the entire inspection apparatus is incorporated in a semiconductor printing apparatus.

A deep-UV light source 1101 comprises an excimer laser or the like. An illuminating system 1102 uniformly and simultaneously illuminates the entire region of a reticle 108 to be inspected from above with a predetermined NA (numerical aperture).

An ultrahigh-resolution lens system (or mirror system) 1109 transfers a reticle pattern onto a wafer 1110. In a printing operation, exposure is performed while shifting the wafer 1110 shot by shot in accordance with a stepping feed of a wafer moving stage 1111. An alignment optical system 1110 aligns the reticle 108 with the wafer 1110 before exposure, and includes at least one microscope system for observing a reticle.

A reticle changer 1114 stores a plurality of reticles to be used. A foreign particle inspection unit 1113 contains all the necessary components of any of the optical systems of the first through fifth embodiments. This unit 1113 inspects foreign particles on the reticle 108 before the reticle 108 is taken out from the reticle changer 1114 and is set at an exposure position (E.P. in FIG. 11).

A controller 1118 controls the basic operation of the stepper, i.e., the sequence of alignment exposure, and stepping movement of the wafer.

Although, in the above-described embodiments, a glass substrate having a pattern on one surface is mainly used as an object to be inspected, except in the case of FIG. 8, the present invention may, of course, be applied to an optical system for inspecting a reticle with dust-proof pellicles affixed thereto, as described, for example, in Japanese Patent Public Disclosure (Kokai) No. 62-219631 (1987).

The present invention may also be applied to an inspection method wherein the horizontal surface of a reticle is twisted relative to the optical system for the purpose of reducing noise due to a circuit pattern, as disclosed in Japanese Patent Public Disclosure (Kokai) No. 62-188943(1987).

By appling the present invention to an apparatus for inspecting a surface state of a substrate, the following effects will be obtained:

(1) Since inspection can be performed by projecting a plurality of light beams onto the surface of a substrate, it is possible to shorten inspection time.

(2) Since inspection by a light beam is not adversely influenced by flare light produced at an edge of a reticle caused by another light beam, reliability in inspection is increased.

Furthermore, by using a first rotating mirror and a second rotating mirror rotated as one body, the present invention also has the effect of reducing the size of a optical system.

WHAT IS CLAIMED IS:

1. An apparatus for inspecting a surface-state of a substrate, comprising:
   a radiation source for emitting a radiation beam;
   means for dividing said radiation beam emitted from said radiation source into a first beam and a second beam;
   a scanning optical system having a scanner for deflecting said first beam to scan a first surface of said substrate and for deflecting said second beam to scan a second surface of said substrate, wherein said scanning optical system is arranged so that when said first beam is incident on the first surface of said substrate, said second beam is not incident on the second surface of said substrate, and when said second beam is incident on the second surface of said substrate, said first beam is not incident on the first surface of said substrate;
   a first light-receiving means for receiving scattered light generated by the incidence of said first beam on the first surface of said substrate; and a second light-receiving means for receiving scattered light generated by the incidence of said second beam on the second surface of said substrate.

2. An apparatus according to claim 1, wherein said scanner comprises a single rotating polygon mirror for reflecting both of said first and second beams.

3. An apparatus according to claim 1, wherein said scanner comprises a plurality of laminated rotating polygon mirrors for reflecting said first and second beams individually.

4. An apparatus according to claim 1, wherein a circuit pattern is formed on the first surface of said substrate, and said first light-receiving means receives scattered light generated by a foreign particle on the first surface of said substrate.

5. An apparatus according to claim 1, wherein said first and second light-receiving means receive reflect-scattered light from said first and second surfaces of said substrate, respectively.

6. An apparatus for exposing a substrate, comprising:
a radiation source for emitting a radiation beam;
means for dividing said radiation beam emitted from said radiation source into a first beam and a second beam;
a scanning optical system having a scanner for deflecting said first beam to scan a first surface of said substrate and for deflecting said second beam to scan a second surface of said substrate, wherein said scanning optical system is arranged so that when said first beam is incident on the first surface of said substrate, said second beam is not incident on the second surface of said substrate, and when said second beam is incident on the second surface of said substrate, said first beam is not incident on the first surface of said substrate;
a first light-receiving means for receiving scattered light generated by the incidence of said first beam on the first surface of said substrate; and
a second light-receiving means for receiving scattered light generated by the incidence of said second beam on the second surface of said substrate.

7. An apparatus according to claim 6, wherein said scanner comprises a single rotating polygon mirror for reflecting both of said first and second beams.

8. An apparatus according to claim 6, wherein said scanner comprises a plurality of laminated rotating polygon mirrors for reflecting said first and second beams individually.

9. An apparatus according to claim 6, wherein said first and second light-receiving means receive reflect-scattered light from said first and second surfaces of said substrate, respectively.

* * * * *

UNITED STATES PATENT AND TRADEMARK OFFICE
CERTIFICATE OF CORRECTION

PATENT NO. : 5,359,407
DATED : October 25, 1994
INVENTOR(S) : Suzuki et al.

It is certified that error appears in the above-indentified patent and that said Letters Patent is hereby corrected as shown below:

COLUMN 6:

Line 17, "3" should read --3)--.
Line 66, "B1" should read --Bℓ--.

COLUMN 8:

Line 53, "Wallaston" should read --Wollaston--.

COLUMN 10:

Line 47,                should read --What is claimed is:--.

Signed and Sealed this

Eleventh Day of April, 1995

Attest:

BRUCE LEHMAN

Attesting Officer        Commissioner of Patents and Trademarks